(12) United States Patent
Beh

(10) Patent No.: US 12,186,978 B2
(45) Date of Patent: Jan. 7, 2025

(54) METHOD OF FORMING A STRUCTURE IN CONTACT WITH AN OBJECT AND A RELATED SYSTEM

(71) Applicant: Agency for Science, Technology and Research, Singapore (SG)

(72) Inventor: Weijie Cyrus Beh, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 150 days.

(21) Appl. No.: 17/924,093

(22) PCT Filed: Apr. 30, 2021

(86) PCT No.: PCT/SG2021/050241
§ 371 (c)(1),
(2) Date: Nov. 8, 2022

(87) PCT Pub. No.: WO2021/230813
PCT Pub. Date: Nov. 18, 2021

(65) Prior Publication Data
US 2023/0271380 A1    Aug. 31, 2023

(30) Foreign Application Priority Data

May 12, 2020   (SG) .......................... 10202004379S

(51) Int. Cl.
*B29C 41/12*    (2006.01)
*A61L 27/06*    (2006.01)
(Continued)

(52) U.S. Cl.
CPC ............ *B29C 64/124* (2017.08); *A61L 27/06* (2013.01); *A61L 27/52* (2013.01); *B29C 64/245* (2017.08);
(Continued)

(58) Field of Classification Search
CPC . B29C 2033/0005; B29C 41/12; B29C 41/20; B29C 64/124; B29C 64/25;
(Continued)

(56) References Cited

U.S. PATENT DOCUMENTS 4,575,330 A * 3/1986 Hull ...................... B29C 64/124
                                                  264/401 X
4,961,154 A * 10/1990 Pomerantz .............. B29C 64/40
                                                  264/401
(Continued)

FOREIGN PATENT DOCUMENTS

CA    3100894 A1    11/2019
JP    62275734 A  * 11/1987    ........... B29C 64/135
(Continued)

OTHER PUBLICATIONS

Translation of JP 62275734 A (published on Nov. 30, 1987).*
(Continued)

*Primary Examiner* — Leo B Tentoni
(74) *Attorney, Agent, or Firm* — Knobbe, Martens, Olson & Bear, LLP

(57) ABSTRACT

There is provided a method of forming a structure that is in contact with an object, the method comprising: (i) supporting a flowable precursor with a flowable support at a position that allows said flowable precursor to be in contact with the object; and (ii) crosslinking at least part of the flowable precursor that is in contact with the object to form a structure that is in contact with the object, wherein a top surface of the part of the flowable precursor that is to be crosslinked, is in interface with a fluid medium. Also provided is a system for performing the method.

19 Claims, 5 Drawing Sheets

(51) Int. Cl.
*A61L 27/52* (2006.01)
*B29C 41/20* (2006.01)
*B29C 64/124* (2017.01)
*B29C 64/245* (2017.01)
*B29C 64/25* (2017.01)
*B29C 64/264* (2017.01)
*B29C 64/40* (2017.01)
*B29C 71/02* (2006.01)
*B29C 71/04* (2006.01)
*B33Y 10/00* (2015.01)
*B33Y 30/00* (2015.01)
*B33Y 80/00* (2015.01)
*B29C 33/00* (2006.01)
*B29K 105/00* (2006.01)
*B29K 105/24* (2006.01)
*B29L 31/00* (2006.01)

(52) U.S. Cl.
CPC ............... *B33Y 10/00* (2014.12); *B33Y 30/00* (2014.12); *B33Y 80/00* (2014.12); *A61L 2420/02* (2013.01); *B29C 2033/0005* (2013.01); *B29K 2105/0061* (2013.01); *B29K 2105/24* (2013.01); *B29L 2031/7532* (2013.01)

(58) Field of Classification Search
CPC ....... B29C 64/264; B29C 64/40; B29C 71/02; B29C 71/04; B29K 2105/24; B33Y 10/00; B33Y 30/00

USPC ......... 264/236, 259, 271.1, 279, 279.1, 298, 264/401, 494; 425/110, 174.4
See application file for complete search history.

(56) References Cited

U.S. PATENT DOCUMENTS

| | | |
|---|---|---|
| 5,248,456 A | 9/1993 | Evans, Jr. et al. |
| 2015/0165678 A1 | 6/2015 | Ding et al. |
| 2016/0046075 A1* | 2/2016 | DeSimone ............ B29C 64/124 264/401 X |
| 2017/0028618 A1 | 2/2017 | Robeson et al. |
| 2018/0243982 A1 | 8/2018 | Shanjani et al. |
| 2019/0160733 A1 | 5/2019 | Mirkin et al. |

FOREIGN PATENT DOCUMENTS

| | | |
|---|---|---|
| WO | WO 2018/182536 A1 | 10/2018 |
| WO | WO 2019/140160 A1 | 7/2019 |
| WO | WO 2021/230813 A1 | 11/2021 |

OTHER PUBLICATIONS

Search Report in corresponding International Patent Application No. PCT/SG2021/050241, dated Jul. 18, 2021, in 4 pages.
Written Opinion in corresponding International Patent Application No. PCT/SG2021/050241, dated Jul. 18, 2021, in 7 pages.

* cited by examiner

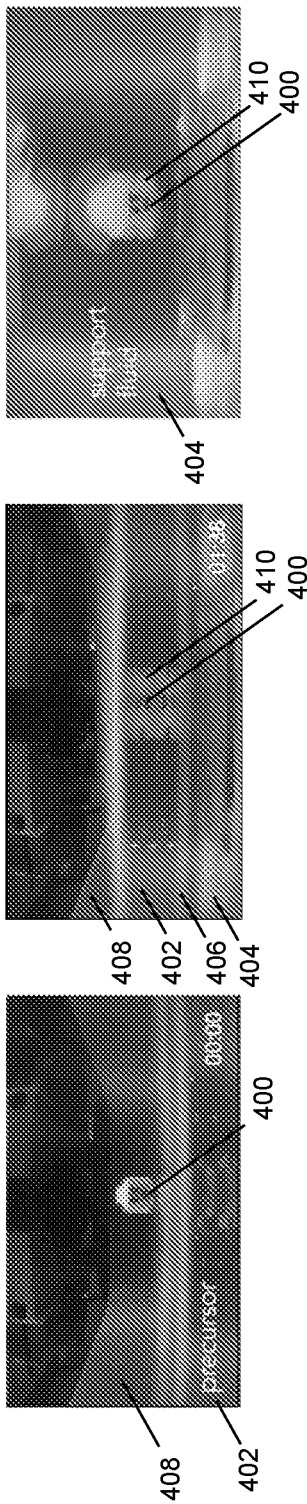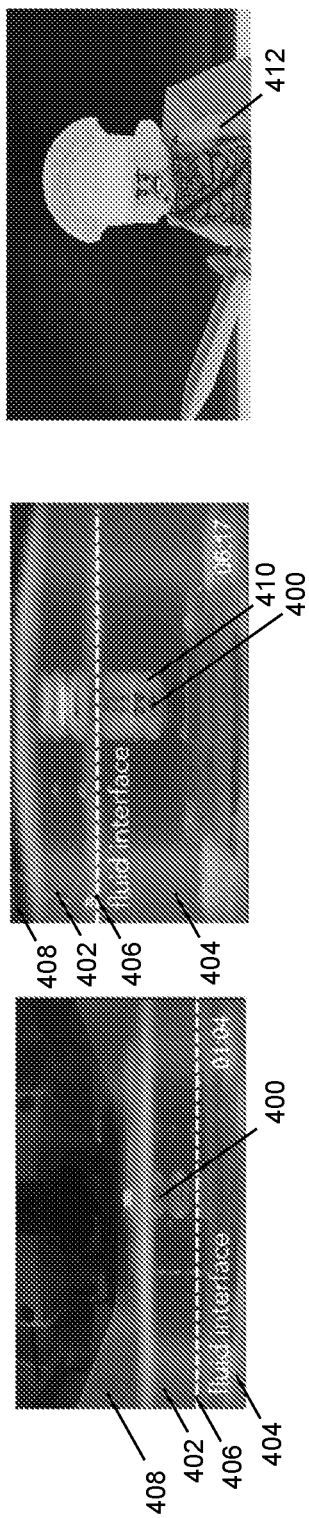
FIG. 4A FIG. 4B FIG. 4C FIG. 4D FIG. 4E FIG. 4F

METHOD OF FORMING A STRUCTURE IN CONTACT WITH AN OBJECT AND A RELATED SYSTEM

TECHNICAL FIELD

The present disclosure relates broadly to a method of forming a structure that is in contact with an object and a related system.

BACKGROUND

Various three-dimensional (3D) printers have been developed thus far. Examples of these 3D printers include extrusion-based printers and resin-based printers. These 3D printers have been proven to be versatile in that they are finding applications in a wide range of technical and non-technical fields. However, it has been recognised that printing of external interfacing layers on or around an object (e.g., a medical device) remains a challenge with existing 3D printers.

In view of the above, there is a need to address at least ameliorate the above-mentioned problem. In particular, there is a need to provide a method of forming a structure that is in contact with an object that address or at least ameliorate the above-mentioned problem.

SUMMARY

In one aspect, there is provided a method of forming a structure that is in contact with an object, the method comprising: (i) supporting a flowable precursor with a flowable support at a position that allows said flowable precursor to be in contact with the object; and (ii) crosslinking at least part of the flowable precursor that is in contact with the object to form a structure that is in contact with the object, wherein a top surface of the part of the flowable precursor that is to be crosslinked, is in interface with a fluid medium.

In one embodiment, the method further comprises (iii) adjusting the position of said top surface relative to the object; (v) further crosslinking at least part of the flowable precursor that is in contact with the object at a new position; and (v) optionally repeating steps (iii) to (iv) until a desired three-dimensional structure that is in contact with the object is formed.

In one embodiment, the step of adjusting the position of said top surface of the part of the flowable precursor that is to be crosslinked comprises adjusting the position of an upper interface of the flowable support relative to the object.

In one embodiment, the step of adjusting the position of the upper interface of the flowable support comprises changing the volume of flowable support.

In one embodiment, the step of adjusting the position of said top surface of the part of the flowable precursor that is to be crosslinked comprises keeping the volume of flowable support constant and changing the position of the object relative to the flowable support.

In one embodiment, at least one crosslinking step is carried out when at least a part of the object is not in contact with both the flowable precursor and the flowable support.

In one embodiment, the flowable precursor is disposed between the flowable support and the fluid medium and interfaces with the fluid medium and the flowable support.

In one embodiment, the crosslinking of the flowable precursor occurs substantially at the interface of the flowable precursor and the fluid medium.

In one embodiment, the flowable support has a density that is higher than that of the flowable precursor and the fluid medium has a density that is lower than that of the flowable precursor.

In one embodiment, crosslinking at least part of the precursor comprises irradiating at least part of the precursor to be crosslinked with an electromagnetic wave.

In one embodiment, the object is coated with an adhesive layer comprising adhesive molecules selected from a group consisting of acrylates, methacrylates, thiols, epoxides, amines, or the like and combinations thereof.

In one embodiment, the flowable precursor comprises at least one polymerizable monomer and at least one photoinitiator.

In one embodiment, the method is a continuous printing method and the step of adjusting the position of said top surface relative to the object is carried out at a rate that substantially matches with the rate the flowable precursor is crosslinked.

In one embodiment, the structure comprises a coating structure.

In one embodiment, the object is a medical device and the coating structure is a hydrogel coating.

In one aspect, there is provided a system for performing the method disclosed herein, the system comprising: a tank containing the flowable precursor, the flowable support and the object; and an irradiation source configured to irradiate the flowable precursor to crosslink at least part of the flowable precursor that is in contact with the object to form a structure that is in contact with the object, wherein a top surface of the part of the flowable precursor that is to be crosslinked, is in interface with a fluid medium.

In one embodiment, the tank comprises an inlet for allowing inflow of the flowable support at a predetermined rate; and an actuator configured to facilitate inflow of the flowable support through the inlet of the tank.

In one embodiment, the system further comprises a processing module configured to adjust the position of said top surface of the precursor relative to the object at a rate that substantially matches with the rate the flowable precursor is crosslinked by the irradiation source.

In one embodiment, the tank is substantially transparent to irradiation from the irradiation source.

In one embodiment, the system is devoid of a screen on top of the flowable precursor.

Definitions

The terms "coupled" or "connected" as used in this description are intended to cover both directly connected or connected through one or more intermediate means, unless otherwise stated.

The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

The term "adjacent" used herein when referring to two elements refers to one element being in close proximity to another element and may be but is not limited to the elements contacting each other or may further include the elements being separated by one or more further elements disposed therebetween.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. It is to be appreciated that the individual numerical values within the range also include integers, fractions and decimals. Furthermore, whenever a range has been described, it is also intended that the range covers and teaches values of up to 2 additional decimal places or significant figures (where appropriate) from the shown numerical end points. For example, a description of a range of 1% to 5% is intended to have specifically disclosed the ranges 1.00% to 5.00% and also 1.0% to 5.0% and all their intermediate values (such as 1.01%, 1.02% . . . 4.98%, 4.99%, 5.00% and 1.1%, 1.2% . . . 4.8%, 4.9%, 5.0% etc.) spanning the ranges. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Furthermore, it will be appreciated that while the present disclosure provides embodiments having one or more of the features/characteristics discussed herein, one or more of these features/characteristics may also be disclaimed in other alternative embodiments and the present disclosure provides support for such disclaimers and these associated alternative embodiments.

DESCRIPTION OF EMBODIMENTS

Exemplary, non-limiting embodiments of a system and a method for forming a structure that is in contact with an object are disclosed hereinafter.

There is provided a method of forming a structure that is in contact or interfaces with an object. The method may comprise: (i) supporting a flowable precursor with a flowable support at a position/level that allows said flowable precursor to be in contact or to interface with the object; and (ii) crosslinking (or curing) at least part of the flowable precursor that is in contact or in interface with the object to form a structure that is in contact or interfaces with the object. Advantageously, the use of support fluid (i.e., said flowable support) in various embodiments allows the use of a relatively small quantity of the precursor (i.e., a thin layer may suffice). Without the support fluid, in principle, a large vat of precursor (i.e., said flowable precursor) may be used. However, this scenario can pose a challenge in that the light used to induce crosslinking can over-crosslink, and cause the printed pattern (i.e., said structure) to be inaccurate, in its size, dimension etc. The scenario also calls for the use of a higher volume of the precursor, since exposure to light will inevitably cause the precursor to start crosslinking and "age", because they are not reusable repeatedly. In various embodiments, the support fluid comprises an inert, reusable support fluid.

In various embodiments, the top surface of the part of the flowable precursor that is to be crosslinked, is in interface with a fluid medium. In various embodiments, the fluid medium may be air, or an inert gas or liquid that for example does not react with the precursor and/or does not react (e.g., crosslink) in the presence of an irradiating source (e.g., ultraviolet radiation). In various embodiments, the fluid medium is also one that allows irradiation to pass through. Further, in various embodiments, the object and structure are composed of different materials such that the structure formed on the object is not merely part of a simple ongoing bulking or building process to add on similar material to an intermediately formed object. Advantageously, in various embodiments, the structure formed on the object may confer additional functions and/or properties to the object as different materials are used. For example, the structure may add mechanical, structural, surface and/or chemical enhancements to the object. In one example, the structure may improve the biocompatibility of the object. In various embodiments, the method is an additive method (i.e., adding or depositing materials to the object) rather than a subtractive method (i.e., removing materials from object e.g., etching).

In various embodiments, the method further comprises (iii) adjusting/changing the position/level of said flowable precursor in contact or in interface with the object; (iv) further crosslinking at least part of the flowable precursor that is in contact or in interface with the object at a new position/level; and (v) optionally repeating steps (iii) to (iv) until a desired three-dimensional structure that is in contact or interfaces with the object is formed. For example, in various embodiments, the method comprises changing the relative position between the precursor and the print bed (e.g., which supports the object), and/or the relative position between the precursor and the object around which printing is performed. The method may also comprise adjusting the position of said top surface of the flowable precursor that is to be crosslinked relative to the object.

In various embodiments, the step of adjusting/changing the position/level of said flowable precursor in contact or in interface with the object comprises adjusting/changing the position/level of the flowable support. For example, the step of adjusting the position of said top surface of the part of the flowable precursor that is to be crosslinked comprises adjusting the position of an upper interface of the flowable support (e.g., a top surface of the flowable support that interfaces with another medium such as the precursor) relative to the object. In various embodiments, the flowable precursor may interface directly with the flowable support or indirectly with one or more intervening intermediate layers disposed between the flowable precursor and the flowable support (e.g., another flowable liquid or separating substrate/solid). The step of adjusting may then additionally also comprise adjusting the position of the intervening intermediate layer(s) with respect to the object. In various embodiments, adjusting the position of an upper interface of the flowable support results in the position/level of any the intervening intermediate layer(s) and/or the position of said top surface of the flowable precursor to change or be adjusted in tandem.

In various embodiments, the step of adjusting/changing the position/level of the flowable support relative to the object comprises raising the level of the flowable support relative to the object (e.g., by increasing the volume of the flowable support and/or by moving the level of a base (such base may be a solid substrate or an intermediate liquid layer) which the flowable support rests on, upwards without changing the volume of the flowable support and/or by moving the object downwards towards the flowable support without changing the volume of the flowable support). In various embodiments, the flowable precursor interfaces with the flowable support, and thus, the step of adjusting may additionally/alternatively comprise adjusting the position of the interface between the flowable precursor and the flowable support.

In various embodiments, the step of adjusting/changing the relative position/level of said flowable precursor in contact or in interface with the object comprises adjusting/changing the position/level of the object. For example, the step of adjusting the position of said top surface of the part of the flowable precursor that is to be crosslinked comprises keeping the volume of flowable support constant and changing the position of the object relative to the flowable support.

In various embodiments, at least one crosslinking step is carried out when at least a part of the object is not in contact with the flowable precursor. For example, the object may be only partially immersed/submerged in the flowable precursor and a portion of the object protrudes or extends out from the flowable precursor. For instance, a part of the object (such as a protrusion) may be exposed to or is in contact with or immersed in the fluid medium, such as air. In various embodiments, the part of the object that is not in contact with the flowable precursor is additionally not in contact with the flowable support. Advantageously, embodiments the method allow for the formation of the structure on an object (e.g., odd-shaped or irregular object) without substantial impediment as embodiments of the method do not require the presence of a rigid plate or screen over the precursor for crosslinking, which may impede/restrict the relative movement of the object from the precursor.

In various embodiments, the flowable precursor is disposed between the flowable support and a fluid medium (e.g., air), for example the flowable precursor interfaces with the flowable support as well as the fluid medium. In various embodiments, the flowable precursor (the entire flowable precursor) may directly interface with the flowable support and the fluid medium, i.e., there are no other intervening layer(s); in other words, the flowable precursor may be in direct contact with the fluid medium and the flowable support, for example, the top surface of the flowable precursor forms an interface with the fluid medium and the bottom surface of the flowable precursor forms an interface with the flowable support. In various embodiments, the flowable precursor interfaces with the flowable support as well as the fluid medium in a configuration as follows: flowable support-flowable precursor-fluid medium. In other words, the flowable precursor may be sandwiched between the flowable support and the fluid medium with no intermediate physical screen/panel (e.g., glass screen) present.

In various embodiments, the method is devoid of a screen or a panel (e.g., glass screen) in contact with the top surface of the flowable precursor and/or in contact with the top surface of a liquid medium (e.g., where the fluid medium is a liquid medium). In other words, in various embodiments, the method is devoid of a constraining substrate positioned over or above the flowable precursor and/or in contact with the top surface of a liquid medium (e.g., if there is one or more liquid medium over the top surface of the flowable precursor, the method may also be devoid of a constraining substrate/panel (e.g., glass screen) over any one of these liquid medium). Advantageously, in various embodiments, the height of the object is not limited by a space between a print bed (e.g., which supports the object) and a top ceiling (e.g., a glass screen that interfaces with the flowable precursor).

In various embodiments, the crosslinking of the flowable precursor occurs at, near, adjacent or in proximity to the interface of the flowable precursor and fluid medium. Advantageously, in various embodiments, only a small amount of flowable precursor or a thin layer of flowable precursor needs to be used at any one time during crosslinking. This reduces wastage of valuable resources while at the same time allowing for better control of structure formation at high resolution and speed. The actual amount of flowable precursor required depends for example on the properties of the precursor (e.g., viscosity, surface tension, etc.) but in various embodiments, as an example, an approximately 3 mm thick layer of the flowable precursor may be used/sufficient in 3D printing a structure.

In various embodiments, the flowable support has a density that is higher than that of the flowable precursor and the fluid medium has a density that is lower than that of the flowable precursor. In various embodiments, the flowable precursor is immiscible with the flowable support and forms separate distinct phases with each other. Advantageously, the flowable support provides the required buoyancy to support the flowable precursor so that it is suitably presented/propped up towards the irradiation source for crosslinking. In various embodiments, the buoyancy of the flowable support is sufficient to support flowable precursor but is insufficient to cause the object to float in/on the flowable support. Hence, in various embodiments, the object is still supported by a print bed. In various embodiments, the flowable support may be an immiscible liquid (with the precursor), and may be selected depending on the flowable precursor. For example, for an aqueous precursor, the flowable support can be a per-fluorinated oil such as FC-40, HFE7500, etc., or an immiscible aqueous solution (i.e., to form an aqueous two-phase system). For common resins (if used as the flowable precursor), the support fluid (or the flowable support) may be water. In various embodiments, one criterion for selecting the flowable support is that the flowable support is denser than the flowable precursor.

In various embodiments, the method comprises forming a structure that at least partially surrounds the object. In some embodiments, the structure fully surrounds the object. In various embodiments, the structure that at least partially surrounds the object tracks or conforms to the contours/outlines of an external surface of the object. In other words, the structure formed may be surrounding and/or be around the object.

In various embodiments, the flowable precursor and the flowable support are each capable of conforming to the contours/outlines of an external surface of the object. For example, the flowable precursor and the flowable support are each capable of conforming to surface contours/outlines having dimensions of no more than about 5 mm, no more than about 4 mm, no more than about 3 mm, no more than about 2 mm, or no more than about 1 mm.

In various embodiments, the method is capable of being carried out on an object with an external surface comprising structural dimensions that are no more than about 5 mm, no more than about 4 mm, no more than about 3 mm, no more than about 2 mm, or no more than about 1 mm. In various embodiments, the object has a complex geometry with intricate surface contours.

In various embodiments, the object is coated with an adhesive layer (e.g., 3-(trimethoxysilyl)propyl methacrylate) that promotes adhesion of the structure to the object. In various embodiments, the adhesive molecules are selected from a group consisting of acrylates, methacrylates, thiols, epoxides, amines, or the like and combinations thereof. In various embodiments, the adhesive molecule is one that can interface between the material to be coated, and the coating material. For example, when the adhesive molecule is 3-(trimethoxysilyl)propyl methacrylate, the trimethoxysilyl group is capable of attaching to metal and glass, and methacrylate is capable of attaching to the acrylate precursor.

In various embodiments, the step of crosslinking at least part of the precursor comprises irradiating at least part of the precursor to be crosslinked with an electromagnetic wave. In various embodiments, the flowable precursor is capable of being crosslinked upon application of an electromagnetic irradiation. The electromagnetic irradiation may include, but not limited to, infra-red waves, ultraviolet waves or electromagnetic waves having wavelengths in the visible light spectrum. In various embodiments, the flowable support is not crosslinkable by application of the same electromagnetic irradiation that crosslinks the flowable precursor. Likewise, in various embodiments, the fluid medium that interfaces with the top of the layer of flowable precursor is not crosslinkable by application of the same electromagnetic irradiation that crosslinks the flowable precursor.

In various embodiments, the electromagnetic irradiation is in the form of a projection onto the flowable precursor from an electromagnetic wave source (e.g., an illumination or irradiating source).

In various embodiments, the projection onto the flowable precursor corresponds to a cross-sectional area of the structure that is to be formed from the crosslinking of the precursor. In various embodiments, the projection (corresponding to the cross-sectional area of the structure to be formed) continuously changes as the position/level of said flowable precursor in contact or in interface with the object changes (e.g., relative to the object) or as the crosslinking occurs.

In various embodiments, the flowable precursor is irradiated at a direction that is substantially perpendicular to the surface of the flowable precursor (e.g., the plane of the flowable precursor-fluid medium interface).

In various embodiments, the flowable precursor is irradiated at a direction that is substantially parallel to the surface of the flowable precursor (e.g., the plane of the flowable precursor-fluid medium interface).

In various embodiments, the method is a continuous printing method and/or a rapid printing method. Various embodiments of the method disclosed herein is can thus be useful in applications such as 3D printing, additive manufacturing, advanced manufacturing and bioprinting of a material (or a structure) that is in contact with an object.

In various embodiments, the step of adjusting/changing the position/level of said flowable precursor is carried out at a rate that substantially matches or is substantially in tandem with (or is substantially proportional to) the rate of crosslinking of the flowable precursor. For example, the step of adjusting the position of said top surface relative to the object is carried out at a rate that substantially matches with the rate the flowable precursor is crosslinked. In various embodiments, the rate of increasing the volume of flowable support and/or the rate of adjusting/changing the position/level of the object matches or is also in tandem with (or is substantially proportional to) the rate of crosslinking of the flowable precursor.

In various embodiments, the flowable precursor comprises at least one polymerizable monomer/crosslinkable polymer and at least one photoinitiator. In various embodiments, the polymer is an acrylate polymer and/or a PEGylated polymer such as PEG-diacrylate (PEGDA). The flowable precursor may comprises polymers of different chain lengths (e.g., from about 100 Da to about 10,000 kDa, from about 200 Da to about 9,500 kDa, from about 300 Da to about 9,000 kDa, from about 400 Da to about 8,500 kDa, from about 500 Da to about 8,000 kDa). In various embodiments, the concentration of polymers is in the range of about 1% to about 50% by weight of the entire flowable precursor. The concentration of the polymers may be in the range of, for example, about 1% to about 50%, about 2% to about 45%, about 3% to about 40%, about 4% to about 35%, and about 5% to about 35%. In various embodiments, the concentration of photoinitiator is in the range of about 0.05% to about 10% by weight of the entire flowable precursor. The concentration of photoinitiator may be in the range of, for example, about 0.05% to about 10%, about 0.065% to about 9%, about 0.08% to about 8%, about 0.095% to about 7%, about 0.11% to about 6%, and about 0.125% to about 5%. In various embodiments, the flowable precursor may be selected from the group consisting of a polymerizable monomer, such as acrylamide, acrylic acid and methacrylates, a crosslinker such as bis-acrylamide and acrylic acid crosslinking species (bi- or multifunctional acrylates, including PEG-diacrylate), or combinations thereof. In various embodiments, the flowable precursor is a hydrogel precursor which is crosslinkable to form a hydrogel.

In various embodiments, the structure comprises a coating structure. As an example, the object may be a medical device and the coating structure can be a hydrogel coating. The medical device may be one that is implantable in the human or animal body and the coating structure may provide enhanced biocompatibility to the medical device.

There is also provided a system for performing the method of forming a structure that is in contact with an object.

In various embodiments, the system comprises a container/tank for holding (or containing) the flowable precursor, the flowable support and the object; and an irradiation source for irradiating (or configured to irradiate) the flowable precursor to crosslink at least part of the flowable precursor that is in contact or in interface with the object to form a structure that is in contact or interfaces with the object, wherein a top surface of the part of the flowable precursor that is to be crosslinked, is in interface with a fluid medium. In various embodiments, the fluid medium may be air, or an inert gas or liquid that does not react to the irradiation and contains one or more properties as herein before described. The fluid medium also allows irradiation to pass through. Further, in various embodiments, the object and structure are of different materials and contain one or more properties as herein before described.

In various embodiments, the container/tank comprises an inlet (i.e., at least one inlet) for allowing inflow of the flowable support at a predetermined rate. The system may further comprise an actuator (e.g., a pump) for facilitating inflow of the flowable support through the inlet of the container/tank. In various embodiments, the container/tank may comprise one or more inlets, and in such embodiments, the actuator may accordingly facilitate inflow of the flowable support through the one or more inlets of the container/tank.

In various embodiments, the system further comprises a processing module configured to adjust the position of said top surface of the flowable precursor relative to the object at a rate that substantially matches with the rate the flowable precursor is crosslinked by the irradiation source. In various embodiments, the processing module may be configured to control, for example, the rate of flow of the flowable support into the container/tank, the intensity of the irradiation by the irradiation source, and the position of the irradiation source etc., to synchronize these parameters that may affect the rate that the position of the top surface of the flowable precursor is adjusted and/or the rate the flowable precursor is crosslinked by the irradiation source. The processing module may also control and determine the type or shape of projection to be irradiated onto the flowable precursor as the relative level (with respect to the object) of the flowable precursor is changed or varied along a vertical axis perpendicular to the top surface of flowable precursor.

In various embodiments, the system further comprises a reservoir for holding a volume of flowable support outside the container/tank. In various embodiments, the reservoir is in fluid communication with the container/tank (e.g., via the inlet(s)).

In various embodiments, the system further comprises a print bed disposed on or in the vicinity of the base of the container/tank. The print bed can support the object which the structure is to be in contact with. In various embodiments, the position of the print bed may also be adjustable (e.g., by the processing module) along a vertical axis perpendicular to the top surface of flowable precursor such that the position of the object relative to the flowable precursor is changed.

In various embodiments, the irradiation source is disposed over the tank/object (e.g., a top-down projection system), under/below the tank/object (e.g., a bottom-up projection system), beside the tank/object (e.g., a side-on projection system) and/or around the tank/object (e.g., a circumferential projection system such as a radial/ring shaped projection system).

In various embodiments, the container/tank is substantially transparent to irradiation from the irradiation source. For example, the container/tank allows transmission of electromagnetic waves emitted from the irradiation source to the flowable precursor. In various embodiments, such a container/tank may be particularly useful when a projection system other than a top-down projection system is used, i.e., when a bottom-up projection system, a side-on projection system, and/or a circumferential projection system is/are used.

In various embodiments, the flowable precursor, the flowable support and the object are disposed within the tank.

In various embodiments, the system is devoid of a screen or a panel (e.g., a glass screen) in contact with the top of (or the top surface of) the flowable precursor. In other words, the system is devoid of a constraining substrate positioned over or above the flowable precursor that limits the thickness of the layer of flowable precursor sandwiched between the constraining substrate and the flowable support. Advantageously, in various embodiments, the height of the object is not limited by a space between a print bed (e.g., which supports the object) and a top ceiling (e.g., a glass screen that interfaces with the flowable precursor). In various embodiments, the tank containing the flowable precursor, the flowable support and the object is an open tank without a cover, thereby exposing the top of the tank and the contents of the tank to air. In some other embodiments, the tank may also contain a cover (e.g., a cover that substantially allows the radiation from the irradiating source to pass through) but the tank also has an unfilled space/volume (i.e., unfilled by liquid or solid matter) below the cover that is still exposed to air. Advantageously, in various embodiments, the configuration of the tank and system allows and provides adequate air space for the positioning of the object and formation of the structure in contact with the object.

In various embodiments, the method and system disclosed herein provide an additive manufacturing technique that utilizes a projection-based system to induce crosslinking of a liquid precursor; utilizes a support fluid that can flow around an existing physical object, and which allows the liquid precursor to be lifted to appropriate heights for patterning; and by combining the two strategies above, allows printing of a new and different material (or structure) around an existing object.

Further, in various embodiments, the method disclosed herein provide a method of three-dimensional (3D) printing around a physical object, having the features of: a projection-based system that induces selective crosslinking of a liquid photocrosslinkable resin or gel precursor; a transfer of support liquid that is immiscible with the liquid resin or gel precursor from a reservoir to the resin tank; and formation of a structure external of a physical object, via the crosslinking of a resin or gel precursor. In various embodiments, the support liquid flows around a physical object and displaces the resin or gel so that patterned crosslinking of said resin or gel precursor can occur at different heights, until the 3D structure surrounding the aforementioned physical object has been completely printed.

In various embodiments, the method and system disclosed herein advantageously allow printing around an existing object since there is no presence of a glass window (i.e., a glass screen or a panel) that limits the objects that can be fitted between the print bed and the glass window.

Further, in various embodiments, the use of a fluid to create a flowing print surface (e.g., the flowable precursor) advantageously allow printing around existing objects.

BRIEF DESCRIPTION OF FIGURES

FIGS. 4A, 4B, 4C, 4D and 4E are screenshots from a video demonstrating the process of printing of a structure (a helmet) around an existing object (a toy figurine), in accordance with various embodiments disclosed herein. FIG. 4F is an image of the printout (the helmet) that was removed from the object (the toy figurine) used in the printing process and placing the printout on another object (another toy figurine).

EXAMPLES

Example embodiments of the disclosure will be better understood and readily apparent to one of ordinary skill in the art from the following discussions and if applicable, in conjunction with the figures. It should be appreciated that other modifications related to structural changes may be made without deviating from the scope of the invention. Example embodiments are not necessarily mutually exclusive as some may be combined with one or more embodiments to form new exemplary embodiments. The example embodiments should not be construed as limiting the scope of the disclosure.

The following examples describe a strategy for non-contact printing, that uses a combination of projection and flowable support materials to print around an existing physical object.

The System

An exemplary system for forming a structure that is in contact with an object is described below with reference to FIG. 1.

Figure 1:
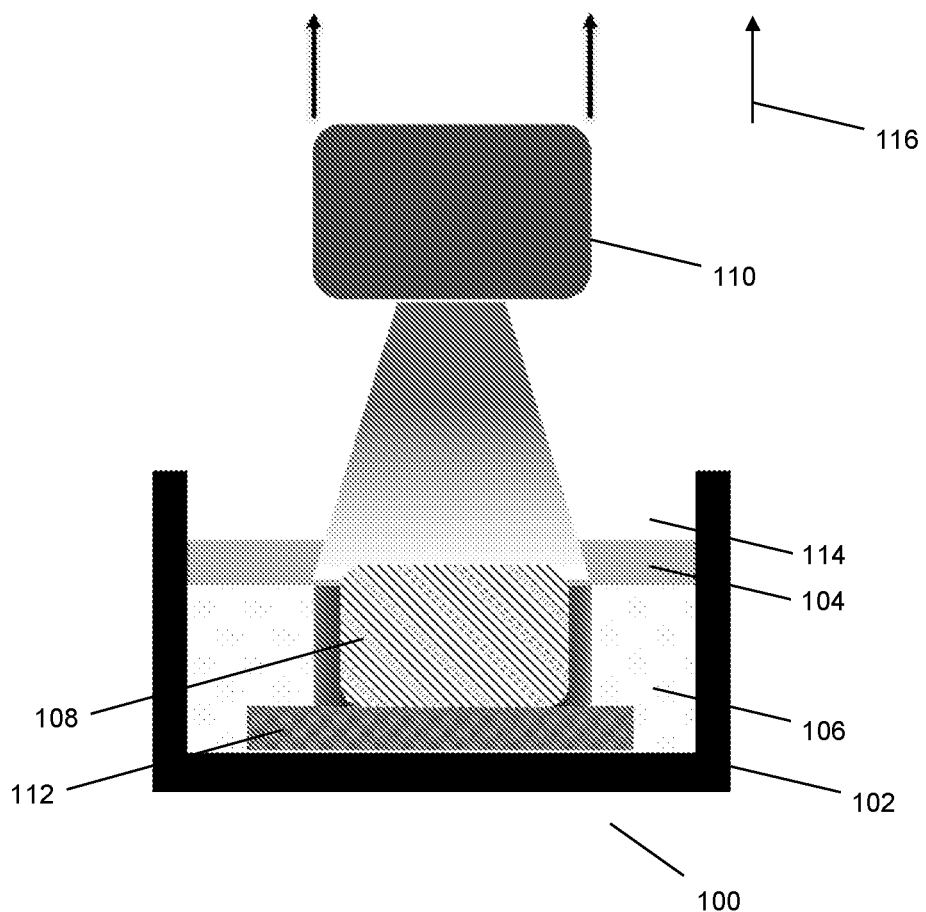
FIG. 1 is a schematic diagram illustrating a side view of a system for forming a structure that is in contact with an object, in accordance with various embodiments disclosed herein.

The system 100 shown in FIG. 1 comprises a tank 102 for holding a flowable precursor 104 forming a precursor layer (e.g., a hydrogel precursor), a flowable support 106 (e.g., a support fluid) and an object 108. The tank 102 is an open tank without a cover/plate over/on the flowable precursor 104. The system 100 of FIG. 1 shows the flowable precursor 104, the flowable support 106 and the object 108 being disposed within the tank 102, wherein the object 108 is disposed on a print bed 112. The top surface of the part of the flowable precursor 104 that is to be crosslinked, is in interface with a fluid medium, which in this case is air 114. The system 100 further comprises an irradiation source 110 (a patterning light source or a projector) for irradiating the flowable precursor 104 to crosslink at least part of the flowable precursor 104 that is in contact or in interface with the object 108 to form a structure that is in contact or interfaces with the object 108.

In the system 100, the flowable precursor 104 comprises a precursor formulation comprising a crosslinkable polymer (e.g., PEG-diacrylate (PEGDA)) and a photoinitiator. The precursor formulation may comprise PEGDA of different chain lengths (500 to 8000 kDa), varying the concentration of both PEGDA (5 to 30%) and a photoinitiator (0.125 to 5%). The precursor formulation may further blend different materials to improve the crosslinking speed, as well as mechanical properties of the final hydrogel. As an example, the precursor formulation may be blended with materials such as alginate, which can be used to increase toughness of the material when multivalent cations are added. Other possible precursor materials may include acrylamide, acrylic acid, methyacrylate, coupled with a suitable crosslinker such as PEG-DA, bis-acrylamide, etc. In the system 100, any suitable photocrosslinkable materials that exist as liquid precursors may be used. In the system 100, as an example, a reasonable crosslinking speed of 2 cm thick 30% PEG500-DA gel in less than 10 minutes can be achieved. Suitable gradient gels may also be fabricated, based on its mechanical properties.

In the system 100, the flowable support 106 is denser than the flowable precursor 104 (the hydrogel precursor), and thereby pushes the flowable precursor 104 upwards to interface with a fluid medium (e.g., air 114). As shown in FIG. 1, in the system 100, the entire top surface of the flowable precursor 104 interfaces with the fluid medium (e.g., air 114).

The flowable support 106 is further able to (or further functions to) prop up any overhanging crosslinked structures (e.g., gel structures) through buoyant forces. This is significant since gel structures can be soft and can collapse under their own weight. The flowable support 106 further does not adhere to the gel structures and thus, the flowable support 106 can be removed by simply rinsing the printout (or the formed 3D structure). Thereby, in the system 100, structures of high geometric complexity can be fabricated.

In the system 100, the tank 102 comprises one or more inlets (not shown) for allowing an inflow of the flowable support 106 at a predetermined rate. The flowable support 106 is provided to the tank 102 at the predetermined rate with the assistance of an actuator, such as a pump (also not shown). The system 100 further comprises a reservoir (also not shown) for holding a volume of the flowable support 106 outside the tank 102 and which is in fluid communication with the tank 102 via the inlet(s). The actuator is configured to facilitate the flow of the flowable support 106 from said reservoir into the tank 102 through the inlet(s) at a predetermined rate. The predetermined rate may be, for example, at a rate that is proportional to the change in the vertical height of the top surface of the flowable precursor 104 in the tank 102. The flowable support 106 is pumped at such a rate to help maintain a thin layer of the flowable precursor 104 that can be crosslinked. This usefully allows continuous crosslinking (i.e., the crosslinking process does not need to be paused to deposit sequential layers of the flowable precursor 104, unlike in stereolithography-based three-dimensional (3D) printers), which is significant for rapid printing.

The system 100 of FIG. 1 shows the print bed 112 being disposed on or in the vicinity of the base of the tank 102. Further, the system 100 of FIG. 1 is shown as being devoid of a screen or a panel (e.g., a glass screen) on top of (or on the top surface of) the flowable precursor 104. In the system 100 of FIG. 1, thereby, the height of the object 108 (which is disposed on the print bed 112 in the system 100) is not limited by the space between the print bed 112 and a top ceiling (e.g., a glass screen that interfaces with the flowable precursor 104). The system 100 thus advantageously allows forming/printing of a structure to take place around an existing object (e.g., object 108) since the support (e.g., flowable support 106) and precursor fluids (e.g., the flowable precursor 104) can flow freely around the object.

In the system 100, adhesion strength of a newly crosslinked material (or structure) to the object can be adjusted by treatment of the object surface with different adhesion molecules, such as 3-(trimethoxysilyl)propyl methacrylate. Alternatively, for snug-fitting prints (or structures), the interfacial friction may be sufficient to anchor the newly printed material (or structure) to the object.

In the system 100 of FIG. 1, the irradiation source 110 is disposed over the tank 102 and the object 108 (i.e., a top-down projection system). The irradiation source 110 projects electromagnetic irradiation along the z-axis (shown by arrow 116) onto the flowable precursor 104, which forms the precursor layer. In the system 100, servo motors are used to translate the irradiation source 110 (i.e., the projector) vertically (in the z-axis, shown by the arrow 116), while the projector sequentially displays cross-sectional slices (or images) of the desired 3D structure (or shape) onto the thin layer of the flowable precursor 104. Different exposure energies can be provided across a single layer by projecting gray levels on the precursor. This results in varying degrees of crosslinking, and hence mechanical strength of the formed 3D structure (e.g., hydrogel coating).

While the exemplary system 100 of FIG. 1 shows a top-down projection system, in alternative examples, a side-on projection system, coupled with appropriate image processing techniques, may be used to achieve a flexible projector and to be able to print certain types of structures, e.g., under over-hung structures in an existing physical object to be printed over. In such alternative examples, Radon transformation, used in imaging systems such as MRI and Computed Tomography, can be repurposed to create projection patterns, that can in turn re-construct a desired 3D structure. Computation will have to be performed by means of different transformation to reconstruct the 3D structure that one intends to fabricate.

Figure 2A:
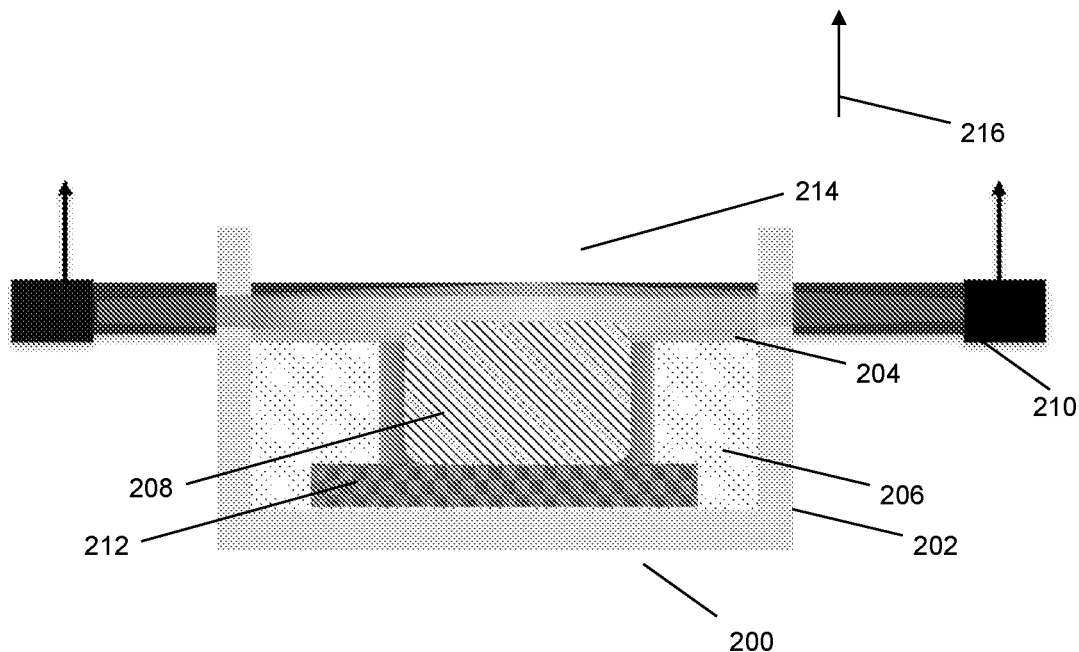
FIG. 2A is a schematic diagram illustrating a side view of an alternative system for forming a structure that is in contact with an object, in accordance with various embodiments disclosed herein.

An alternative exemplary system with a side-on projection system is described below with reference to FIG. 2A. In FIG. 2A, similar to the system 100 shown in FIG. 1, the system 200 comprises a tank 202 for holding a flowable precursor 204, a flowable support 206 and an object 208. The system 200 further comprises an irradiation source 210 for irradiating the flowable precursor 204. The system 200 also comprises a print bed 212 disposed on or in the vicinity of the base of the tank 202. In the system 200, the object 208 is disposed on the print bed 212. Further, the flowable precursor is in interface with a fluid medium (e.g., air 214).

In the system 200 of FIG. 2A, the tank 202 is transparent to irradiation from the irradiation source 210. Further, the irradiation source 210 (or the projector) is in the form of a side-on projection system and is in the particular form of a ring-shaped array of projection elements, such as laser diodes, that moves vertically in lock-step with the flowable precursor 204 (i.e., a precursor layer). That is, in this form, with the ring-shaped projector or diode array, a translation along the z-axis (shown by arrow 216) will suffice. As shown in FIG. 2A, as the irradiation source 210 (or the projector) moves along the z-axis (shown by the arrow 216), patterns are projected radially inward from outside a transparent print-tank 202. The tank 202 allows transmission of electromagnetic waves emitted from the irradiation source 210 to the flowable precursor 204.

Figure 2B:
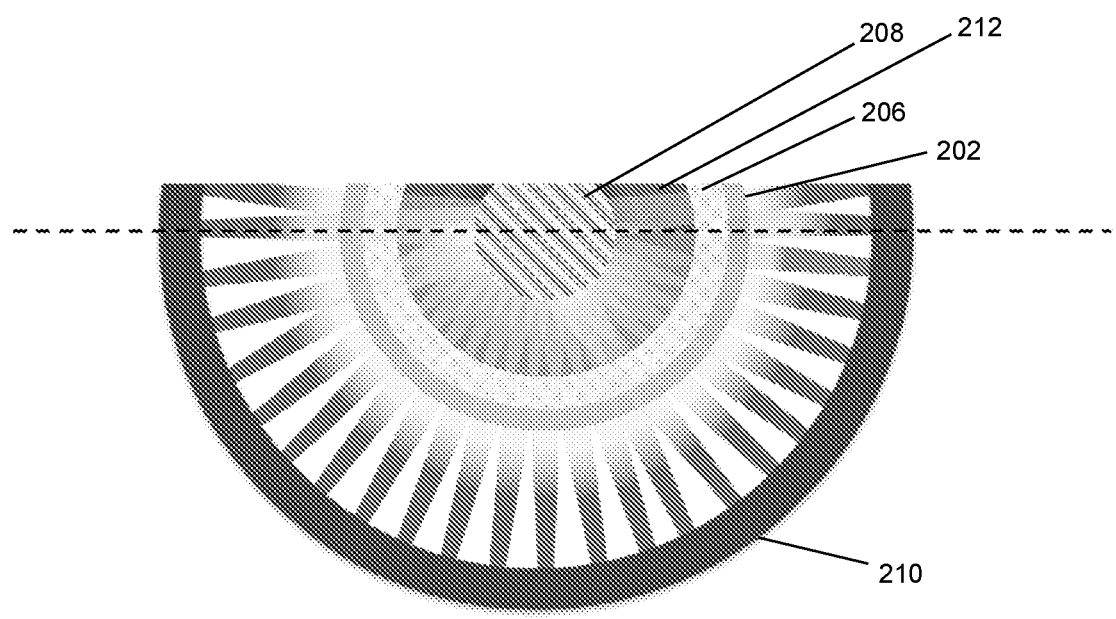
FIG. 2B is a schematic diagram illustrating a top view of the alternative system, in accordance with various embodiments disclosed herein.

See also FIG. 2B which shows a top view of the system 200 of FIG. 2A. In a further alternative example, the side-on projection system may be in the form of a single projector travelling in a helical fashion, with sufficient overlap in the z-axis to provide proper coverage. That is, the irradiation source (or the projector) may be set on a revolving platform and may proceed via a helical path to illuminate different regions of the flowable precursor. In either form (i.e., a ring-shaped projector that translates along the z-axis or a single projector travelling in a helical fashion), by devising manufacturability rules to optimize the printing performance and adopting a suitable projection method, the resulting system (i.e., a 3D printer) may advantageously even be able to print over structures that are over-hung in the radial direction.

In other alternative examples, a combination of various projection systems (i.e., with different projection directions) may be adopted to increase the versatility of a system.

The various examples of the system described above may usefully facilitate a projected printing technique to fabricate around existing objects. The systems described not only can be used for typical 3D printing applications, but the systems use a contact-free printing method that permits printing around existing objects. By illuminating the regions around an existing object, gelation can be induced selectively around the object (e.g., an implant) to form the desired structure around that object. Modifications of the systems (or the printers), as well as optimization of the printing conditions, may be performed to achieve the desired 3D structure.

Figure 3A:
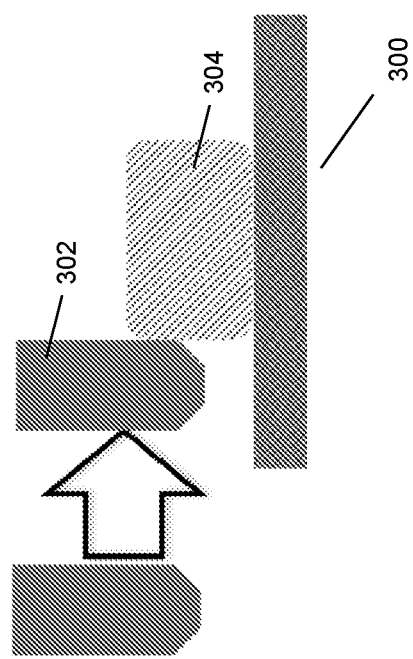
FIGS. 3A, 3B and 3C are schematic diagrams illustrating obstruction caused by a nozzle in an extrusion-based three-dimensional (3D) printer, obstruction caused by scraper in a stereolithography-based 3D printer, and contact-free projected printing.
Figure 3B:
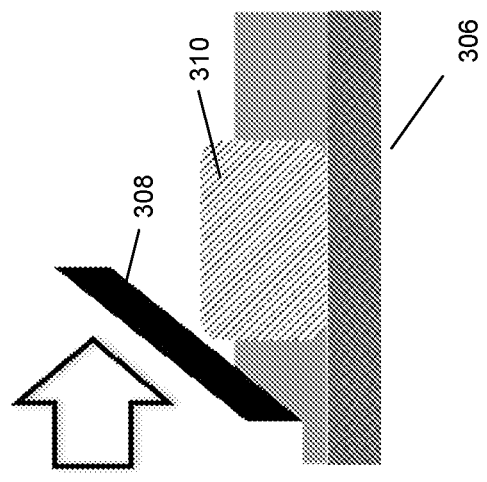
Figure 3C:
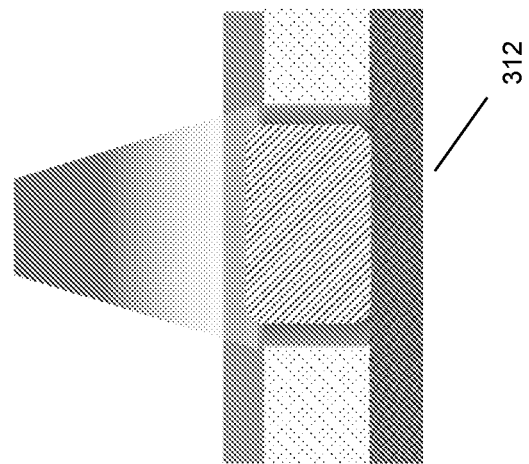

The various examples of the system described may also usefully minimise having physical components that may hinder printing around an existing object. For example, in the various examples described, it may be possible to avoid the issue of nozzle movement being obstructed if an extrusion-based 3D printer 300 is used, as shown in FIG. 3A (see the moving precursor nozzle 302, the movement shown by the rightward arrow, obstructed by an object 304, e.g., an implant, in FIG. 3A). In the various examples described, it may be possible to also avoid the issue of the precursor layering mechanism being obstructed if a stereolithography-based 3D printer 306 is used, as shown in FIG. 3B (see the moving precursor scraper 308, the movement shown by the rightward arrow, obstructed by an object 310, e.g., an implant, in FIG. 3B). Therefore, various examples of the system described may make printing around an object (e.g., an implant) easier than in extrusion and stereolithography-based 3D printers for example. In the various examples described, by using a contact-free printing strategy 312 as shown in FIG. 3C, the 3D printing approach described would be able to encapsulate an object (e.g., an implant) in a hydrogel coating (e.g., a printed 3D structure) with minimal difficulty.

The various examples of the system described may be configured to be cell compatible, which may be useful for biomedical applications for example.

The Method

An exemplary method for forming a structure that is in contact with an object is described below with reference to FIGS. 4A, 4B, 4C, 4D, 4E and 4F. These figures illustrate the various stages of the exemplary method applied to 3D printing a helmet around a toy figurine.

As shown in FIG. 4A, the head of a toy figurine 400 is placed inside a print tank, on a print bed (compare object 108 disposed on print bed 112 in tank 102 of FIG. 1). FIG. 4A also shows a precursor 402 (compare flowable precursor 104 of FIG. 1). The precursor shown in FIG. 4A is floated on top of a support fluid (see support fluid 404 shown in FIG. 4B, below a fluid interface 406 between the precursor 402 and the support fluid 404; compare flowable support 106 of FIG. 1) and the top surface of the part of the precursor that is to be crosslinked is in interface with a fluid medium (e.g., air; see air 408). In FIG. 4A, the precursor 402 is supported with the support fluid 406 at a position that allows said precursor 402 to be in contact with the toy figurine 400. At this stage, at least part of the precursor 402 that is in contact with the toy figurine 400 is crosslinked to form a part of a structure (i.e., a helmet in this example) that is in contact with the toy figurine 400. The crosslinking is induced upon irradiation.

Next, as shown in FIG. 4B, the position of the top surface of the precursor 402 relative to the object (the toy figurine 400) is adjusted (i.e., the precursor 402 is raised/lifted) to a new, suitable position (or level) by the support fluid 406 as the support fluid 406 is pumped into the print tank. The white dashed line shown in FIG. 4B indicates the interface 406 between the support and precursor layer (i.e., between the precursor 402 and the support fluid 406). Simultaneously, an image corresponding to a cross-sectional area/pattern of the desired printout at the new position (or level or height) is projected onto the top of the precursor 402, and at least part of the precursor 402 that is in contact with the toy figurine 400 is further crosslinked at the new position in the process. These steps described with reference to FIG. 4B is repeated until the helmet (i.e., the desired 3D structure) that is in contact with the toy figurine 400 is formed.

After around 30 seconds (compare time stamps shown at the bottom right of FIGS. 4B and 4C), as shown in FIG. 4C, the initial layer of the helmet 410 is completed (printed), and this initial layer serves as an anchor on which the rest of the printout will be built.

As shown in FIG. 4D, the support fluid 404 is raised continuously (i.e., the position of the top surface of the precursor 402 relative to the object/toy figurine 400 is raised (or lifted) as images corresponding to a cross-sectional area/pattern of the desired printout at each new position are projected onto the top of the precursor 402.

As shown in FIG. 4E, upon completion (i.e., when the helmet 410 is fully printed), the printed structure 410 is submerged (or fully immersed) in the support fluid 404. The printout 410 can then be removed from the toy figurine 400 as, in this example, adhesion-promoting molecules were not coated on the head of the toy figurine 400 prior to printing. The removed helmet can then be transferred onto another toy figurine 412, as shown in FIG. 4F.

In the exemplary method described above, advantageously, the use of the support fluid allows the use of a relatively small quantity of the precursor (i.e., a thin layer of the precursor would suffice). If, instead of using the support fluid, a large vat of the precursor is used, this poses a challenge in that the light causing the crosslinking of the precursor can over-crosslink and cause the printed pattern to be inaccurate.

Further to the above, in the exemplary method described above, the top surface of the part of the precursor that is to be crosslinked is in interface with a fluid medium (e.g., air). That is, the method is devoid of a screen (e.g., a glass screen) or a panel in contact with the top surface of the part of the precursor that is to be crosslinked. Advantageously, in the exemplary method described, the height of the object (e.g., the toy figurine 400) is not limited by a space between a print bed and a top ceiling (e.g., a glass screen that interfaces with the precursor).

3D-Printed Hydrogel Coatings

One potential application of the present disclosure is to perform 3D printing around implants. Various medical implants have titanium alloy casings, which are relatively inert. However, these materials are prone to recognition by the immune system, resulting in fibrous encapsulation in a process known as foreign body reaction (FBR). By 3D printing hydrogel coatings around a titanium implant, the hydrogel coating may be used to modulate the immune response, by presenting a much softer structure that does not cause mechanical stress to the surrounding tissues; creating a non-fouling surface that prevents recognition by the immune system; and serving as a reservoir to store anti-inflammatory and anti-fibrotic drugs. To achieve these effects, the hydrogels should adhere well to the titanium implant.

Experiments were carried out to test hydrogel adhesion under different conditions. For the purposes of the experiments, two titanium grades—CP6 and Ti6Al4V—are used because they have been utilized in implants. The hydrogel tested is polyethylene glycol diacrylate (PEGDA), which has been used in various biomedical applications due to its low fouling properties.

Titanium plates are cleaned with atmospheric plasma (3 minutes), followed by incubation with a methacrylated silane (methacryloyl propyl trimethoxysilane) (50% v/v in ethanol) for 45 minutes. The silane serves as anchoring molecule, with which the hydrogel will react to create a covalent bond. After airdrying, PEGDA with 1 mM lithium phenyl-2,4,6-trimethylbenzoylphosphinate (LAP) photoinitiator (i.e., the hydrogel precursor) is dispensed between a glass plate, and either a treated or untreated titanium plate, with a 1 mm spacer, and photocrosslinked with an LED light source. The glass-gel-titanium assembly is then subject to lap shear test. See the lap shear test setup 500 shown in FIG. 5A, with the glass plate 502 and the titanium plate 504 positioned at opposite ends of the setup 500 and with the hydrogel precursor 506 sandwiched between one end of the glass plate 502 and one end of the titanium plate 504, forming the glass-gel-titanium assembly. The lap shear test consists of a tensile test on the glass-gel-titanium assembly, where the shear stresses cause the hydrogel 506 to debond from the titanium surface of the titanium plate 504.

Figure 5B:
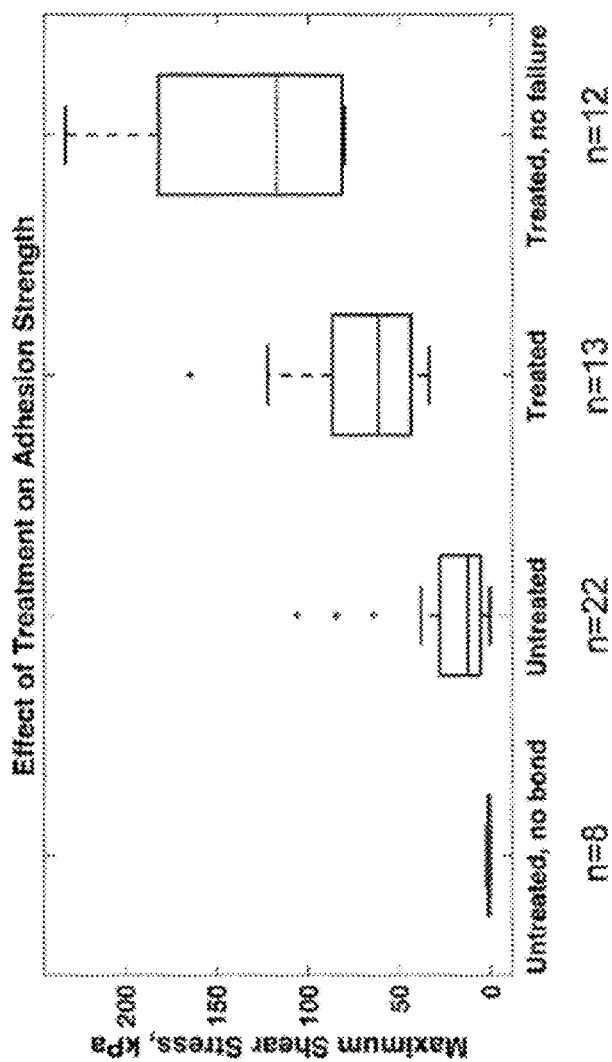
FIG. 5B is a box and whisker plot showing the effect of treatment on adhesion strength in accordance with various embodiments disclosed herein.
Figure 5A:
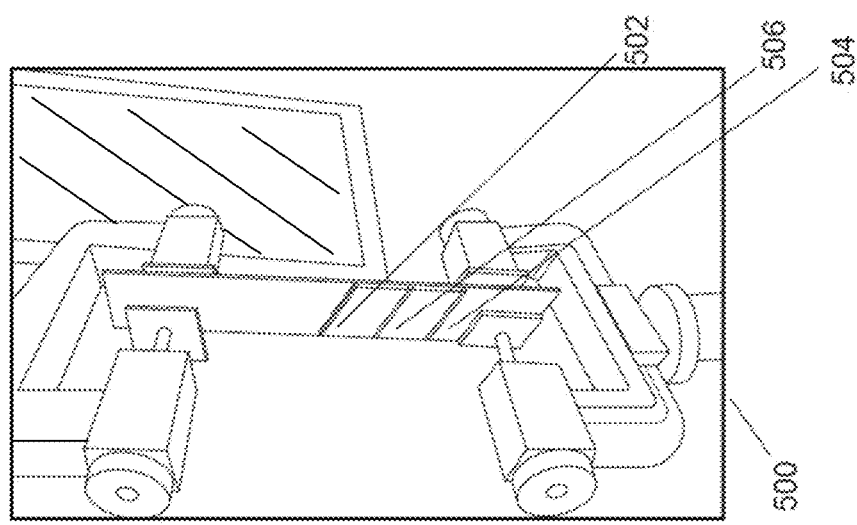
FIG. 5A is an image showing a lap shear test setup (to test hydrogel adhesion), in accordance with various embodiments disclosed herein.

As shown in the box and whisker plot of FIG. 5B showing the effect of treatment on adhesion strength, when compared with the untreated titanium samples (columns 1 and 2, counting from the left of FIG. 5B), the treated samples (columns 3 and 4, counting from the left of FIG. 5B) are able to attain demonstrably greater strength.

From the experiments (e.g., see FIG. 5B), the treatment of the titanium surface with the silane results in improved mechanical strength, with about half the samples never failing even at the upper force limit of the mechanical tester. These results show that the modification of the titanium plates can help to achieve robust adhesion of the hydrogel coating, which is a significant property for implant coating applications.

APPLICATIONS

Advantageously, various embodiments of the system and the method disclosed herein provide a means to fabricate arbitrary shapes around existing physical objects using flowable support.

Even more advantageously, various embodiments of the system and method disclosed herein can be utilized in a number of technical applications, including interfacing layers for medical implants, which are often much stiffer than the surrounding tissues, and can thus cause irritation. In a related application, various embodiments of the system and method disclosed herein can be used to fabricate customized interfacing components to go around standard components, such as electronics (e.g., smart devices) and strength-imparting supports (e.g., in prosthetics).

Various embodiments of the system and method disclosed herein usefully allow for the combination of manufactured components, such as electronics, with custom designed parts (e.g., personalized layers for better fit and comfort) with little compromise in terms of interfacing, sealing, etc.

It will be appreciated by a person skilled in the art that other variations and/or modifications may be made to the embodiments disclosed herein without departing from the spirit or scope of the disclosure as broadly described. For example, in the description herein, features of different exemplary embodiments may be mixed, combined, interchanged, incorporated, adopted, modified, included etc. or the like across different exemplary embodiments. The present embodiments are, therefore, to be considered in all respects to be illustrative and not restrictive.

The invention claimed is:

1. A method of forming a structure that is in contact with an object, the method comprising:
   (i) supporting a flowable precursor with a flowable support at a position that allows said flowable precursor to be in contact with the object; and
   (ii) crosslinking at least part of the flowable precursor that is in contact with the object to form a structure that is in contact with the object,
   wherein a top surface of the part of the flowable precursor that is to be crosslinked, is in interface with a fluid medium,
   wherein at least one crosslinking step is carried out when at least a part of the object is not in contact with the flowable precursor and not in contact with the flowable support.

2. The method as claimed in claim 1, further comprising:
   (iii) adjusting a position of said top surface relative to the object;
   (iv) further crosslinking at least part of the flowable precursor that is in contact with the object at a new position; and
   (v) optionally repeating steps (iii) to (iv) until a desired three-dimensional structure that is in contact with the object is formed.

3. The method as claimed in claim 2, wherein the step of adjusting the position of said top surface of the part of the flowable precursor that is to be crosslinked comprises adjusting a position of an upper interface of the flowable support relative to the object.

4. The method as claimed in claim 3, wherein the step of adjusting the position of the upper interface of the flowable support comprises changing the volume of flowable support.

5. The method as claimed in claim 3, wherein the step of adjusting the position of said top surface of the part of the flowable precursor that is to be crosslinked comprises keeping the volume of flowable support constant and changing a position of the object relative to the flowable support.

6. The method as claimed in claim 1, wherein the flowable precursor is disposed between the flowable support and the fluid medium and interfaces with the fluid medium and the flowable support.

7. The method as claimed in claim 6, wherein the crosslinking of the flowable precursor occurs substantially at the interface of the flowable precursor and the fluid medium.

8. The method as claimed in claim 1, wherein the flowable support has a density that is higher than that of the flowable precursor and the fluid medium has a density that is lower than that of the flowable precursor.

9. The method as claimed in claim 1, wherein crosslinking at least part of the precursor comprises irradiating at least part of the precursor to be crosslinked with an electromagnetic wave.

10. The method as claimed in claim 1, wherein the object is coated with an adhesive layer comprising adhesive molecules selected from a group consisting of acrylates, methacrylates, thiols, epoxides, amines, and combinations thereof.

11. The method as claimed in claim 1, wherein the flowable precursor comprises at least one polymerizable monomer and at least one photoinitiator.

12. The method as claimed in claim 2, wherein the method is a continuous printing method and the step of adjusting the position of said top surface relative to the object is carried out at a rate that substantially matches with the rate the flowable precursor is crosslinked.

13. The method as claimed in claim 1, wherein the structure comprises a coating structure.

14. The method as claimed in claim 13, wherein the object is a medical device and the coating structure is a hydrogel coating.

15. A system for forming a structure that is in contact with an object, the system comprising:
   a tank containing a flowable precursor and a flowable support; and
   an irradiation source configured to irradiate the flowable precursor to crosslink at least part of the flowable precursor that is in contact with the object to form a structure that is in contact with the object,
   wherein a top surface of the at least part of the flowable precursor that is to be crosslinked, is in interface with a fluid medium, and
   wherein the object is positioned in a tank and configured such that at least a part of the object is not in contact with the flowable precursor and not in contact with the flowable support during at least one crosslinking step of the at least part of the flowable precursor.

16. The system as claimed in claim 15, wherein the tank comprises an inlet for allowing inflow of the flowable support at a predetermined rate; and an actuator configured to facilitate inflow of the flowable support through the inlet of the tank.

17. The system as claimed in claim 15, further comprising a processing module configured to adjust a position of said top surface of the precursor relative to the object at a rate that substantially matches with the rate the flowable precursor is crosslinked by the irradiation source.

18. The system as claimed in claim 15, wherein the tank is substantially transparent to irradiation from the irradiation source.

19. The system as claimed in claim 15, wherein the system is devoid of a screen on top of the flowable precursor.

* * * * *